# (12) United States Patent
Flach et al.

(10) Patent No.: US 8,082,042 B2
(45) Date of Patent: Dec. 20, 2011

(54) ELECTRODE DEVICE FOR ELECTRODIAGNOSIS AND/OR ELECTROTHERAPY

(75) Inventors: Erhard Flach, Berlin (DE); Wolfgang Geistert, Rheinfelden (DE); Gernot Kolberg, Berlin (DE); Michelle Maxfield, Berlin (DE); Ingo Weiss, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 785 days.

(21) Appl. No.: 11/742,366

(22) Filed: Apr. 30, 2007

(65) Prior Publication Data
US 2008/0004680 A1    Jan. 3, 2008

(30) Foreign Application Priority Data
Jun. 28, 2006 (DE) .......... 10 2006 029 864

(51) Int. Cl.
*A61N 1/05*    (2006.01)
(52) U.S. Cl. ........ 607/116; 607/115; 607/117; 607/118; 607/119; 607/122
(58) Field of Classification Search .......... 607/115–119, 607/122
See application file for complete search history.

(56) References Cited

U.S. PATENT DOCUMENTS

| | | | |
|---|---|---|---|
| 4,198,991 A | 4/1980 | Harris | |
| 4,945,342 A | 7/1990 | Steinemann | |
| 5,265,579 A | 11/1993 | Ferrari | |
| 5,411,527 A * | 5/1995 | Alt | .................................... 607/5 |
| 5,433,730 A | 7/1995 | Alt | |
| 5,554,176 A | 9/1996 | Maddison et al. | |
| 5,683,444 A | 11/1997 | Huntley et al. | |
| 5,824,026 A * | 10/1998 | Diaz | .............................. 607/116 |
| 5,938,597 A | 8/1999 | Stratbucker | |
| 2004/0064175 A1* | 4/2004 | Lessar et al. | ................... 607/122 |
| 2005/0222658 A1 | 10/2005 | Hoegh et al. | |

FOREIGN PATENT DOCUMENTS

| | | |
|---|---|---|
| DE | 263239 | * 12/1988 |
| DE | 263239 A | 12/1988 |
| DE | 10217828 | 10/2003 |
| DE | 10217828 A1 | 10/2003 |
| EP | 1354610 | 10/2003 |
| FR | 2446001 | 8/1980 |
| GB | 1219017 | * 1/1971 |
| WO | WO 2005/053555 A1 | 6/2005 |
| WO | WO 2005/116702 | 6/2005 |
| WO | WO 2005/116702 | 12/2005 |
| WO | WO2005053555 | 12/2005 |

OTHER PUBLICATIONS

German Search Report, dated Jan. 29, 2007.
European Search Report, dated Dec. 20, 2007.

* cited by examiner

*Primary Examiner* — Niketa Patel
*Assistant Examiner* — Rex R Holmes
(74) *Attorney, Agent, or Firm* — ARC IP Law, PC; Joseph J. Mayo

(57) ABSTRACT

An electrode device for cardiological or neurological electrodiagnosis and/or electrotherapy comprises an elongated electrode body (12), at least one electrode (14, 16) in the vicinity of the distal end (24) of the electrode body (12), and an electrode conductor (44) for the electrical connection of the electrode (14, 16). The electrode conductor (44) has a fibrous structure (52) with anisotropic conductivity so that the specific conductivity of the electrode conductor (44) is significantly higher in its longitudinal direction than in its transverse direction.

28 Claims, 2 Drawing Sheets

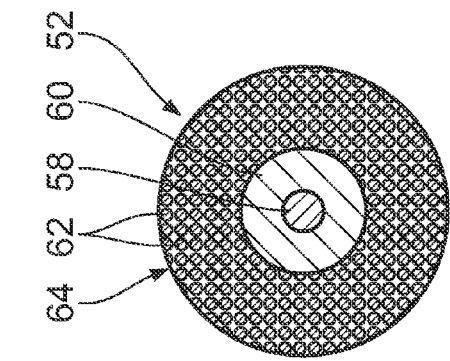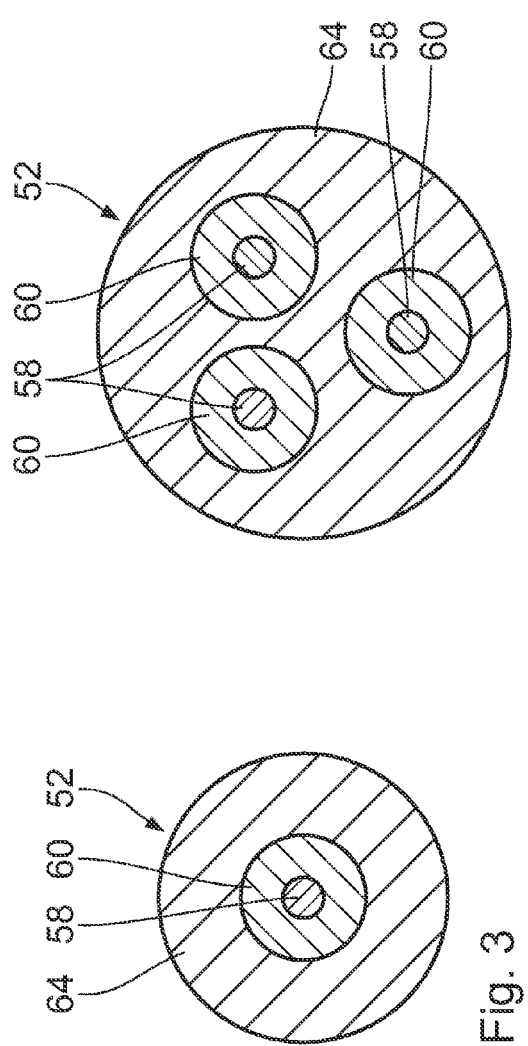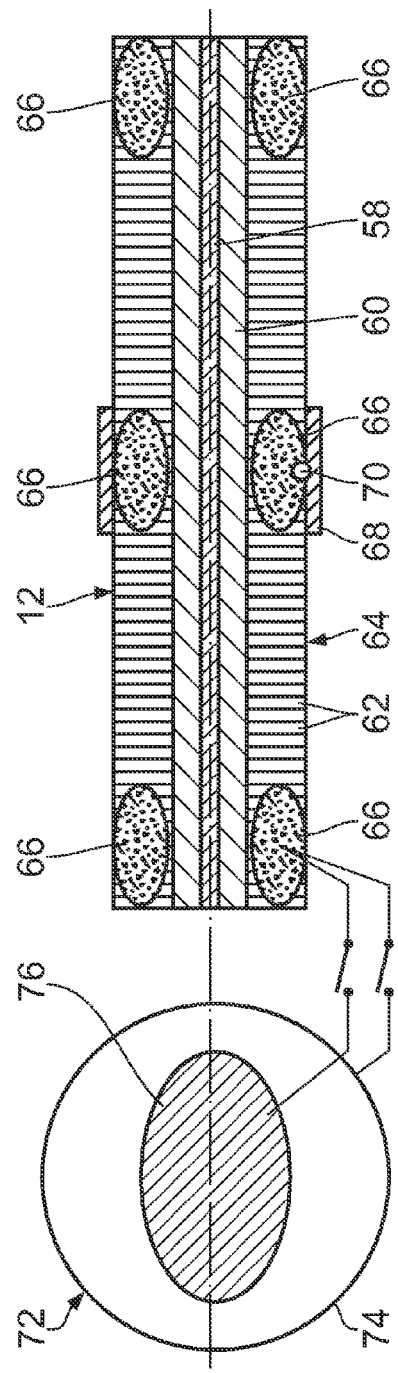

ELECTRODE DEVICE FOR ELECTRODIAGNOSIS AND/OR ELECTROTHERAPY

This application takes priority from German Patent Application DE 10 2006 029 864.0 filed 28 Jun. 2006, the specification of which is hereby incorporated herein by reference.

BACKGROUND OF THE INVENTION

1. Field of the Invention

The invention relates to an electrode device for cardiological or neurological electrodiagnosis and/or electrotherapy.

2. Description of the Related Art

Such electrode devices are disclosed, for example, in WO 2005/053555 A1. They are used in the field of electrophysiology, particularly for the detection and treatment of conduction disturbances in the heart and nervous system, and they are also known as stimulation, pacemaker or ICD electrodes or as EP catheters (electrophysiology catheters). They have an elongated electrode body which is provided on or in front of its distal end with at least one electrode. The later may, for example, be a sensing electrode for sensing cardiological or neuronal signals, an ablation electrode for the local sclerosis of cardiac tissues, or a therapy electrode for the emission of electrical stimulation signals, for example signals from a neurostimulator, heart pacemaker or defibrillator. The electrode(s) are each provided with an electrode conductor for its (their) electrical connection to a corresponding basic unit, such as an electrical generator, an electrotherapy unit or an implant such as a neurostimulator, a heart pacemaker or defibrillator.

Conventional electrode devices, such as those known from the state of the art in many different embodiments, use solid, metal feed lines or cords as electrode conductors, where the individual conductors are not insulated from each other. A patient who has implanted such an electrode device is excluded from gentle magnetic resonance diagnosis using core spintomographs since such metal electrode conductors may overheat in extremely strong electromagnetic fields such as those generated in magnetic resonance tomographs (MRT's) due to the flowing induction currents or the surrounding layers of tissue due to induction currents escaping at the ends of the conductors.

A method is also disclosed in the above-mentioned WO 2005/053 555 A1 for forming the electrode conductors from carbon fibers comprising a multiplicity of filaments. Although this provides a certain improvement relative to solid metal supply lines or cords, the conducting characteristics of such electrode conductors, in terms of their applicability in strong magnetic fields, requires further improvement.

SUMMARY OF THE INVENTION

The object of the invention is therefore to optimize an electrode device for electrodiagnosis and/or electrotherapy for operation in the MR tomograph.

This object is achieved by a fibrous structure of the electrode conductor with anisotropic conductivity. Here the specific conductivity of the electrode conductor, in its longitudinal direction, is significantly higher than in its transverse direction. "Significantly higher" means in this context that the anisotropy of the specific conductivity, matched to the dimensions of the electrode conductor itself and the strength and nature of the magnetic field used in MR tomography will be selected so that when the electrode device is used in MR tomography, no physiologically harmful heating of the electrode conductor takes place.

According to a preferred exemplary embodiment the fibrous structure may consist of a solid fiber composite based, for example, on an elongated fiber bundle, and of a bundle of individual fibers. The latter may be formed by loosely juxtaposed, twisted, braided, glued, pressed or otherwise bundled filaments.

To achieve the anisotropic conductivity of the electrode conductor it is particularly effective if the fibers themselves have an anisotropic conductivity that is significantly higher in the longitudinal direction than in the transverse direction. For this purpose each individual fiber may, because of the manufacturing process, be designed so that their conductivity gradually decreases radially from inside to outside due to the intrinsic material properties. Simpler to achieve, however, is a fiber structure in which a high resistance to insulating surface layer of fibers is produced. This surface layer may be formed by a material conversion of the fiber material itself, and consists, for example, of high resistance residues formed during the conversion of polymer fibers in carbon fibers due to intense heating. Alternatively, a surface layer separate from the actual fiber material may be formed by a surface reaction, for example oxidation, of the fiber material.

The application of a separate coating as a high resistance to insulating surface layer can also be easily controlled from the point of view of process engineering. This coating may be applied by dipping, spraying, steaming and physical or chemical precipitation.

In principle all sufficiently conductive materials that can be applied mechanically in a suitable form, such a carbon, metals, conducting plastics (such as those known from capacitors with a solid electrolyte) or semiconductor materials are suitable for the fibers of the electrode device.

BRIEF DESCRIPTION OF THE DRAWINGS

Further features, details and advantages of the invention are evident from the following description, in which an exemplary embodiment is explained in further detail with reference to the attached drawings, in which:

FIG. 6 shows a longitudinal section through an electrode body in a further embodiment with an implant illustrated diagrammatically.

DETAILED DESCRIPTION OF THE INVENTION

Figures 1, 2:
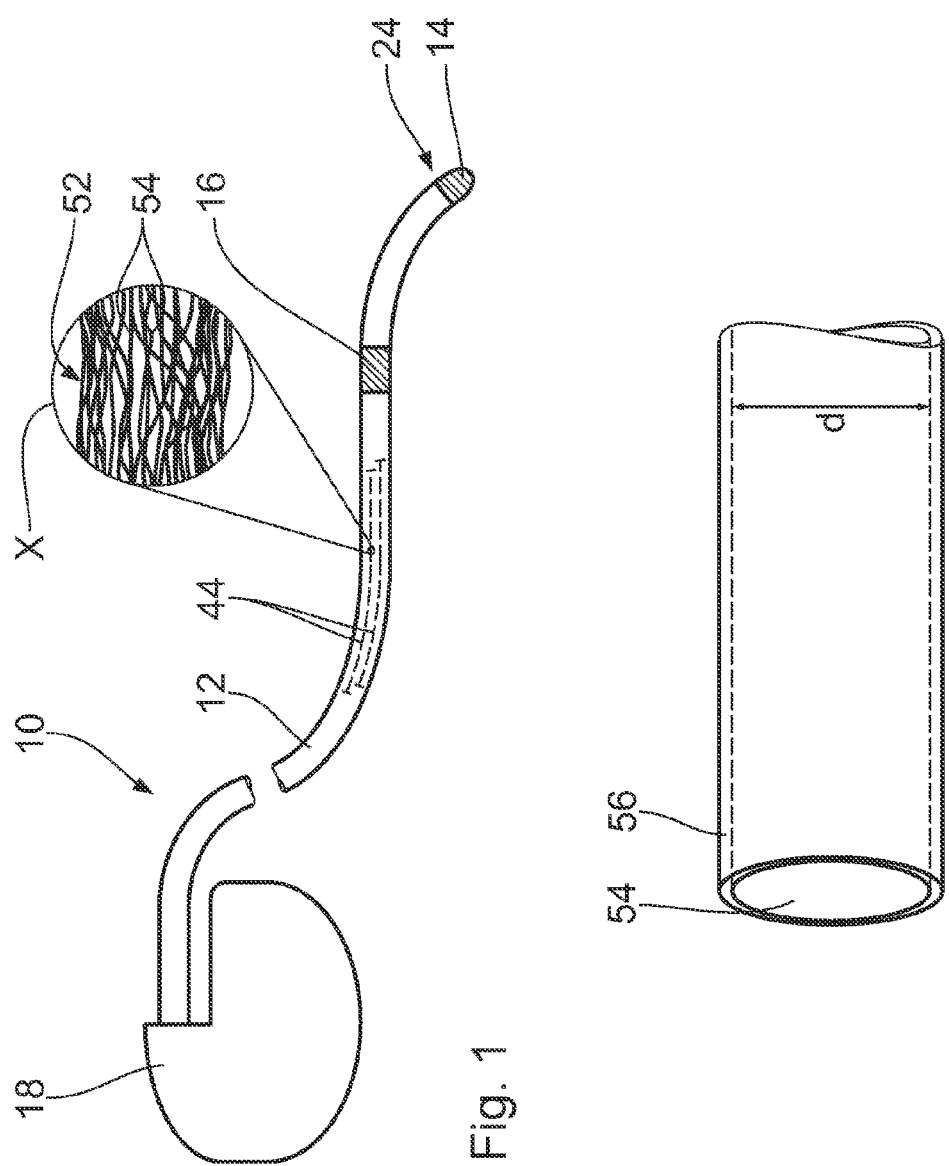
FIG. 1 shows an explanatory sketch of a bipolar electrode device with an enlarged detailed section of the electrode conductor.
FIG. 2 shows a sectional view of an individual fiber of the electrode conductor according to FIG. 1, FIG. 3 to 5 show cross-sections through electrode conductors in further exemplary examples.

FIG. 1 shows diagrammatically an electrode device in the form of a functional electrostimulator device 10. This is provided on the one hand with an elongated electrode body 12, which supports on its distal end 24 two electrodes, namely a tip electrode 14 and a ring electrode 16. Tip electrode 14 and ring electrode 16 serve to detect hear signals and emit stimulation pulses to surrounding tissue. On the other hand electrostimulator 10 has a housing 18 which contains the components required for the functionality of electrostimulator 10, such as a pulse generator, electrical circuits and an energy supply.

Electrode body 12 has at its proximal end, i.e. the end connected to housing 18, suitable structures not shown in greater detail here, which enable a connection to be made to housing 18. Such structures are sufficiently known from the state of the art and have no further significance as far as this invention is concerned. A detailed description of the same is therefore dispensed with.

Tip and ring electrodes 14, 16 represent electrically conducting structural elements which comprise a transition point for electrical energy to the cardiac tissue. Ring electrode 16 may consist of a platinum-iridium alloy, whilst distal tip electrode 14 has a hemispherical head consisting of an iridium-coated platinum-iridium alloy. Electrodes 14, 16 may be designed as discharge, stimulation or measuring electrodes and may be varied to a large extent in terms of material, number, position and geometry without this being relevant to the object of this invention.

Electrode conductors 44 (indicated by dotted lines in FIG. 1) are also embedded in electrode body 12, which conductors make the electrical connection of electrodes 14, 16 to the corresponding functional components in housing 18.

As is evident from the sectional detailed enlargement in FIG. 1 and FIG. 2, denoted by X, electrode conductor 44 is formed from a fibrous structure consisting of a bundle 52 of individual fibers 54 of carbon. These individual fibers 54 run with their main direction of extension essentially parallel to the longitudinal direction of electrode conductor 44, and are bundled in a loose, only moderately arranged position by a plastic, not shown in further detail in FIG. 1.

As is clear from FIG. 2, individual fibers 54 are provided with an insulating surface layer 56, which may, for example, be of a sprayed on, non-conducting polymer. Individual fibers 54 have a diameter d between a few μm and a few tenths of a millimeter. Several hundred to several ten thousand insulated individual fibers 54 form electrode conductor 44 so that it has a highly anisotropic conductivity. The specific conductivity in the longitudinal direction is higher by at least one order of magnitude than in its transverse direction. A current fed in the longitudinal direction of electrode conductor may then flow unobstructed through fiber bundle 52 to tip electrode 14, whilst a magnetic field acting from outside encounters more difficult induction conditions. This applies particularly when electrode conductor 44 is not stretched but curved in a magnetic field.

In the embodiments of the invention shown in FIGS. 3 to 5, an anisotropically conducting fiber bundle is constructed from different types of materials. Thus a fiber bundle may consist of a combination of two or more materials such as metal fibers, carbon fibers, conducting plastic fibers and semi-conducting fibers, preference being given to a combination of materials of varying conductivity. In all cases these are insulated or almost insulated individual fibers, as mentioned above. In the exemplary embodiment according to FIGS. 3 and 4 the better (longitudinally) conducting fibers 58, positioned as the core of the bundle, are surrounded by less conducting fibers 60 with conventional insulation. In a preferred exemplary embodiment the (longitudinal) conductivity of the enclosing fibers gradually decreases radially. In a further exemplary embodiment with combined fiber materials the fibers of higher conductivity are distributed uniformly among the other fibers. An application example is the provision of an ICD electrode feed line in which highly conducting silver cords are combined with carbon fibers.

A further embodiment of the invention according to FIG. 5 is based on the use of active and passive fibers. Active fibers are understood to mean those which connect the implant electronics to the electrodes, i.e. transmit energy or signals for the electrotherapy or diagnosis. In the above text these active fibers 58, 60 are always referred to. Passive fibers 62 differ from them in that they are not used for electrotherapy but serve only to screen irradiated electromagnetic energy. Here the fibrous structure will reduce the depth of penetration due to the anisotropically conducting fiber structure. In the preferred design such fibers fill the insulation volume as completely as possible, i.e. these longitudinally conducting fibers 62, which are if possible insulated transversally from each other, pass through electrode jacket 64, consisting of silicon, for example. Insulating jacket 64 is in this case only transversally insulating and is longitudinally conducting. The objective here is to render the entire cross-section longitudinally conducting. Similarly this structure corresponds in terms of the longitudinal conductor to a conductor with a large cross-sectional radius (the entire lumen is rendered longitudinally conducting), which, as is known, is heated to a lesser degree in electromagnetic alternating fields.

In a further exemplary embodiment according to FIG. 6 these passive fibers 62 are connected galvanically to each other at least one end (e.g. with a conducting adhesive), and therefore have the possibility of connecting a merging node 66 close to the implant permanently, or only in a certain operating mode of implant 72, to implant housing 74 and/or implant electronics 76. In an expanded version a plurality of merging nodes 66 of passive fibers 62 distributed over electrode body 12 are obtained, which nodes are permanently connected, or only connected in a certain operating mode of the implant, to conductive structures on the jacket of electrode body 12. These may, for example, be ring electrodes or coils 68, which have galvanic contact with the body fluid and which are not used for therapy at or only temporarily. Contact point 70 may also be designed as a switch which only temporarily connects the ring electrodes or coils 68.

A further exemplary embodiment uses as passive fibers those which are not continuous throughout the electrode conductor length. Here the fiber structure has a felt-like structure with a preferred direction in the longitudinal axis of electrode conductor 44. This is based on the fact that the reflection characteristics of the screen felt can be optimized for the undesirable frequency of the electromagnetic radiation by adjusting the diameter length ratio of the individual fibers.

What is claimed is:

1. An electrode device for cardiological or neurological electrodiagnosis and/or electrotherapy, comprising:
   an electrode body (12) that is elongated;
   at least one electrode (14, 16) in the vicinity of a distal end (24) of said electrode body (12);
   an electrode conductor (44) for electrical connection of said at least one electrode (14, 16) wherein said electrode conductor (44) comprises a fibrous structure (52) with anisotropic conductivity wherein a specific conductivity of said electrode conductor (44) is significantly higher in a longitudinal direction along said electrode conductor than in a transverse direction across said electrode conductor;
   wherein said fibrous structure (52) comprises individual fibers (54) comprising a fiber material wherein said individual fibers (54) comprise a plastic, conducting plastic or semiconductor material and wherein said individual fibers (54) have an insulating surface layer (56) that comprises a high resistance and wherein said insulating surface layer comprises said fiber material;
   wherein said insulating surface layer further comprises high resistance residues of said fiber material,
   or
   an oxidized portion of said fiber material;

wherein said fibrous structure comprises a solid fiber composite or a bundle said individual fibers (54); and, wherein said bundle has centrally highly conducting fibers (58) which are surrounded by less highly conducting fibers (60), wherein longitudinal conductivity of said highly conducting fibers (60) gradually decreases radially.

2. The electrode device according to claim 1, wherein said solid fiber composite comprises an elongated fiber bundle.

3. The electrode device according to claim 1, wherein said bundle of said individual fibers (54) comprises loosely juxtaposed, twisted, braided, glued or pressed filaments.

4. The electrode device according to claim 1, wherein said individual fibers themselves have an anisotropic significantly higher conductivity in a longitudinal direction along said individual fibers than in a transverse direction across said individual fibers.

5. The electrode device according to claim 1, wherein said fibrous structure comprises individual fibers (54) in a number between several tens and several ten thousands.

6. The electrode device according to claim 1, wherein said fibrous structure (52) comprises a combination of two or more materials.

7. An electrode device for cardiological or neurological electrodiagnosis and/or electrotherapy, comprising:
   an electrode body (12) that is elongated;
   at least one electrode (14, 16) in the vicinity of a distal end (24) of said electrode body (12);
   an electrode conductor (44) for electrical connection of said at least one electrode (14, 16) wherein said electrode conductor (44) comprises a fibrous structure (52) with anisotropic conductivity wherein a specific conductivity of said electrode conductor (44) is significantly higher in a longitudinal direction along said electrode conductor than in a transverse direction across said electrode conductor;
   wherein said fibrous structure comprises a solid fiber composite or a bundle of individual fibers (54); and,
   wherein said solid fiber composite or said bundle has centrally highly conducting fibers (58) which are surrounded by less highly conducting fibers (60), wherein longitudinal conductivity of said highly conducting fibers (60) gradually decreases radially.

8. The electrode device according to claim 7, wherein said solid fiber composite comprises an elongated fiber bundle.

9. The electrode device according to claim 7, wherein said bundle of individual fibers (54) comprises loosely juxtaposed, twisted, braided, glued or pressed filaments.

10. The electrode device according to claim 7, wherein said individual fibers themselves have an anisotropic significantly higher conductivity in a longitudinal direction along said individual fibers than in a transverse direction across said individual fibers.

11. The electrode device according to claim 7, wherein said fibrous structure (52) comprises individual fibers (54) that have an insulating surface layer (56) that comprises a high resistance.

12. The electrode device according to claim 11, wherein said surface layer comprises an oxidized material.

13. The electrode device according to claim 11, wherein said high resistance to insulating surface layer (56) comprises an applied coating.

14. The electrode device according to claim 7, wherein said fibrous structure comprises individual fibers (54) in a number between several tens and several ten thousands.

15. The electrode device according to claim 7, wherein said individual fibers (54) comprise a plastic, a metal, conducting plastic or semiconductor material.

16. The electrode device according to claim 7, wherein said fibrous structure (52) comprises a combination of two or more materials.

17. The electrode device according to claim 7, wherein said bundle comprises:
   active fibers (58); and,
   passive fibers (62).

18. The electrode device according to claim 17, further comprising an insulating jacket wherein said passive fibers (62) are contained within said insulating jacket (64).

19. The electrode device according to claim 18, wherein said passive fibers (62) are galvanically connected to each other at least one end of said passive fibers in a merging node (66).

20. The electrode device according to claim 19, wherein said merging node (66) is configured to connect to an implant housing (18) or implant electronics or to an implant housing and implant electronics.

21. The electrode device according to claim 19, further comprising a plurality of said merging nodes (66) of said passive fibers (62), distributed over said elongated electrode body (12).

22. The electrode device according to claim 21, wherein said electrode conductor comprises a jacket having conducting structures and wherein said plurality of merging modes (66) distributed over said electrode body (12) are electrically connected to said conducting structures on said jacket of said electrode conductor (44).

23. The electrode device according to claim 17, wherein said passive fibers (62) do not extend continuously throughout a length of said electrode conductor.

24. An electrode device for cardiological or neurological electrodiagnosis and/or electrotherapy, comprising:
   an electrode body (12) that is elongated;
   at least one electrode (14, 16) in the vicinity of a distal end (24) of said electrode body (12);
   an electrode conductor (44) for electrical connection of said at least one electrode (14, 16) wherein said electrode conductor (44) comprises a fibrous structure (52) with anisotropic conductivity wherein a specific conductivity of said electrode conductor (44) is significantly higher in a longitudinal direction along said electrode conductor than in a transverse direction across said electrode conductor;
   wherein said fibrous structure (52) comprises individual fibers (54) comprising a fiber material wherein said individual fibers (54) comprise a plastic, conducting plastic or semiconductor material and wherein said individual fibers (54) have an insulating surface layer (56) that comprises a high resistance and wherein said insulating surface layer comprises said fiber material;
   wherein said insulating surface layer further comprises high resistance residues of said fiber material,
      or
      an oxidized portion of said fiber material;
   wherein said fibrous structure comprises a solid fiber composite or a bundle said individual fibers (54);
   wherein said bundle comprises:
      active fibers (58);
      passive fibers (62);
   an insulating jacket wherein said passive fibers (62) are contained within said insulating jacket (64); and, wherein said passive fibers (62) are galvanically connected to each other at least one end of said passive fibers in a merging node (66).

25. The electrode device according to claim 24, wherein said merging node (66) is configured to connect to an implant housing (18) or implant electronics or to an implant housing and implant electronics.

26. The electrode device according to claim 24, further comprising a plurality of said merging nodes (66) of said passive fibers (62), distributed over said elongated electrode body (12).

27. The electrode device according to claim 26, wherein said electrode conductor comprises a jacket having conducting structures and wherein said plurality of merging modes (66) distributed over said electrode body (12) are electrically connected to said conducting structures on said jacket of said electrode conductor (44).

28. The electrode device according to claim 24, wherein said passive fibers (62) do not extend continuously throughout a length of said electrode conductor.

* * * * *